US012042499B2

(12) United States Patent
Ecsedy et al.

(10) Patent No.: US 12,042,499 B2
(45) Date of Patent: Jul. 23, 2024

(54) ADMINISTRATION OF AURORA KINASE INHIBITOR AND CHEMOTHERAPEUTIC AGENTS

(71) Applicant: Millennium Pharmaceuticals, Inc., Cambridge, MA (US)

(72) Inventors: Jeffrey A. Ecsedy, Newton, MA (US); Mengkun Zhang, Walpole, MA (US)

(73) Assignee: Millennium Pharmaceuticals, Inc., Cambridge, MA (US)

(*) Notice: Subject to any disclaimer, the term of this patent is extended or adjusted under 35 U.S.C. 154(b) by 0 days.

(21) Appl. No.: 16/838,684

(22) Filed: Apr. 2, 2020

(65) Prior Publication Data

US 2020/0397799 A1    Dec. 24, 2020

Related U.S. Application Data

(62) Division of application No. 15/746,008, filed as application No. PCT/US2016/043041 on Jul. 20, 2016, now abandoned.

(60) Provisional application No. 62/195,103, filed on Jul. 21, 2015.

(51) Int. Cl.
| | | |
|---|---|---|
| A61K 31/55 | (2006.01) | |
| A61K 31/282 | (2006.01) | |
| A61K 33/243 | (2019.01) | |
| A61P 35/00 | (2006.01) | |

(52) U.S. Cl.
CPC .......... *A61K 31/55* (2013.01); *A61K 31/282* (2013.01); *A61K 33/243* (2019.01); *A61P 35/00* (2018.01); *A61K 2300/00* (2013.01)

(58) Field of Classification Search
CPC .... A61K 31/55; A61K 31/282; A61K 33/243; A61K 2300/00; A61P 35/00
See application file for complete search history.

(56) References Cited

U.S. PATENT DOCUMENTS

| | | | |
|---|---|---|---|
| 4,099,012 A | 7/1978 | Gschwend | |
| 4,469,633 A | 9/1984 | Trybulski | |
| 4,481,142 A | 11/1984 | Fryer et al. | |
| 5,166,151 A | 11/1992 | Freidinger et al. | |
| 5,210,082 A | 5/1993 | Bock et al. | |
| 6,057,329 A | 5/2000 | Davis et al. | |
| 6,277,844 B1 | 8/2001 | Spector et al. | |
| 6,727,251 B2 | 4/2004 | Bebbington et al. | |
| 7,572,784 B2 | 8/2009 | Claiborne et al. | |
| 7,718,648 B2 | 5/2010 | Claiborne et al. | |
| 8,026,246 B2 | 9/2011 | Claiborne et al. | |
| 8,399,659 B2 | 3/2013 | Claiborne et al. | |
| 9,102,678 B2 | 8/2015 | Claiborne et al. | |
| 9,765,076 B2 | 9/2017 | Claiborne et al. | |
| 9,765,078 B2 | 9/2017 | Claiborne et al. | |
| 9,988,384 B2 | 6/2018 | Claiborne et al. | |
| 2003/0022885 A1 | 1/2003 | Bebbington et al. | |
| 2003/0055068 A1 | 3/2003 | Bebbington et al. | |
| 2005/0032839 A1 | 2/2005 | Fancelli et al. | |
| 2005/0256102 A1 | 11/2005 | Claiborne et al. | |
| 2006/0074074 A1 | 4/2006 | Ohtsuka et al. | |
| 2006/0160874 A1 | 7/2006 | Tonani et al. | |
| 2007/0142368 A1 | 6/2007 | Xiao et al. | |
| 2007/0185087 A1 | 8/2007 | Claiborne et al. | |
| 2008/0045501 A1 | 2/2008 | Claiborne et al. | |
| 2008/0167292 A1 | 7/2008 | Claiborne et al. | |
| 2009/0142337 A1 | 6/2009 | Squires | |
| 2009/0299060 A1 | 12/2009 | Claiborne et al. | |
| 2010/0310651 A1 | 12/2010 | Mittal | |
| 2011/0033461 A1 | 2/2011 | Ratushny et al. | |
| 2011/0039826 A1 | 2/2011 | Ramanan et al. | |
| 2011/0245234 A1 | 10/2011 | Armitage et al. | |
| 2011/0312942 A1 | 12/2011 | Claiborne et al. | |
| 2014/0046055 A1 | 2/2014 | Claiborne et al. | |
| 2014/0336180 A1 | 11/2014 | Chakravarty et al. | |
| 2015/0166545 A1 | 6/2015 | Claiborne et al. | |
| 2018/0134716 A1 | 5/2018 | Claiborne et al. | |
| 2018/0207173 A1 | 7/2018 | Ecsedy et al. | |

FOREIGN PATENT DOCUMENTS

| | | |
|---|---|---|
| EP | 0014470 A2 | 8/1980 |
| EP | 0273697 A2 | 7/1988 |
| WO | WO-97/19065 A1 | 5/1997 |
| WO | WO-97/32883 A1 | 9/1997 |
| WO | WO-98/28281 A1 | 7/1998 |
| WO | WO-98/058926 A1 | 12/1998 |
| WO | WO-00/67754 A1 | 11/2000 |
| WO | WO-02/068415 A1 | 9/2002 |
| WO | WO-02/094834 A1 | 11/2002 |
| WO | WO-03/013545 A1 | 2/2003 |

(Continued)

OTHER PUBLICATIONS

Rossi et al. Journal of Clinical Oncology, 2012, vol. 30, No. 14, pp. 1692-1698.*
Golub et al., Science, vol. 286, Oct. 15, 1999, pp. 531-537.*
Blair et al., Abstract A282: Antitumor activity of alisertib (MLN8237), an investigational small molecule Aurora A kinase inhibitor, as a single agent and in combination with paclitaxel, in experimental models of small cell lung cancer, (2013), Mol Cancer Ther, 12, A282 (Year: 2013).*
Pujol et al. (Jun. 6, 2000), Is there a case for cisplatin in the treatment of small-cell lung cancer? A meta-analysis of randomized trials of a cisplatin-containing regimen versus a regimen without this alkylating agent, British Journal of Cancer, 83, 8-15 (Year: 2000).*
U.S. Appl. No. 15/996,166, Claiborne et al.

(Continued)

*Primary Examiner* — Kortney L. Klinkel
*Assistant Examiner* — Dawanna Shar-Day White
(74) *Attorney, Agent, or Firm* — Jones Day (57) ABSTRACT

Disclosed are methods for the treatment of cancer in patients in need of such treatment. The methods comprise administering to such a patient an Aurora kinase inhibitor such as 4-{[9-chloro-7-(2-fluoro-6-methoxyphenyl)-5H-pyrimido [5,4-d][2]benzazepin-2-yl]amino}-2-methoxybenzoic acid or a pharmaceutically acceptable salt in combination with a platin. Also disclosed are medicaments for use in the treatment of cancer.

10 Claims, 3 Drawing Sheets

(56) References Cited

FOREIGN PATENT DOCUMENTS

| WO | WO-2004/000833 A1 | 12/2003 |
| --- | --- | --- |
| WO | WO-2004/043953 A1 | 5/2004 |
| WO | WO-2004/058781 A1 | 7/2004 |
| WO | WO-2004/071507 A1 | 8/2004 |
| WO | WO-2005/002552 A2 | 1/2005 |
| WO | WO-2005/002576 A2 | 1/2005 |
| WO | WO-2005/005427 A1 | 1/2005 |
| WO | WO-2005/013996 A2 | 2/2005 |
| WO | WO-2005/037843 A1 | 4/2005 |
| WO | WO-2005/118544 A2 | 12/2005 |
| WO | WO-2006/003440 A1 | 1/2006 |
| WO | WO-2005/111039 A3 | 4/2006 |
| WO | WO-2006/036266 A1 | 4/2006 |
| WO | WO-2006/055528 A2 | 5/2006 |
| WO | WO-2006/055561 A2 | 5/2006 |
| WO | WO-2006/055831 A2 | 5/2006 |
| WO | WO-2006/070192 A1 | 7/2006 |
| WO | WO-2006/070195 A1 | 7/2006 |
| WO | WO-2006/070198 A1 | 7/2006 |
| WO | WO-2006/070202 A1 | 7/2006 |
| WO | WO-2007/056164 A2 | 5/2007 |
| WO | WO-2007/076348 A2 | 7/2007 |
| WO | WO-2007/113212 A2 | 10/2007 |
| WO | WO-2007/132220 A1 | 11/2007 |
| WO | WO-2007/132221 A1 | 11/2007 |
| WO | WO-2007/132228 A1 | 11/2007 |
| WO | WO-2008/021038 A2 | 2/2008 |
| WO | WO-2008/063525 A1 | 5/2008 |
| WO | WO-2010/134965 A1 | 11/2010 |
| WO | WO-2011/014248 A1 | 2/2011 |
| WO | WO-2017/015316 A1 | 1/2017 |

OTHER PUBLICATIONS

A Phase 1 Dose Escalation Study of MLN8237, an Aurora A Kinase Inhibitor, in Adult Patients With Nonhematological Malignancies, Followed by Phase 2 of MLN8237 in Lung, Breast, Head and Neck, or Gastroesophageal Malignancies, <http://clinicaltrials.gov/archive/NCT01045421/2012_01_30> (2012).

Alvarez, R.H. et al., MLN8237 (alisertib), an investigational Aurora A Kinase inhibitor, in patients with breast cancer: Emerging phase 2 results, Cancer Research, 72(24 suppl. 3): 543s, 6 pages, (2012).

Bischoff, J.R. et al., A homologue of *Drosophila aurora* kinase is oncogenic and amplified in human colorectal cancers, European Molecular Biology Organization, 17(11):3062-3065 (1998).

Cancer Prevention Overview, National Cancer Institute, 2 pages, (Last modified Aug. 31, 2009).<http://www.cancer.gov/cancertopics/pdq/prevention/overview/patient>. Retrieved on Apr. 9, 2010.

Cantor, E.H. et al., Interaction of calcium channel blockers with non-neuronal benzodiazepine binding sites, Proceedings of the National Academy of Sciences, 81:1549-1552 (1984).

Carmena, M. et al., The Cellular Geography of Aurora Kinases, Nature, 4:842-854 (2003).

Cervantes, A. et al., Phase I pharmacokinetic/pharmacodynamic study of MLN8237, an investigational, oral, selective aurora a kinase inhibitor, in patients with advanced solid tumors, Clin. Cancer Res., 18(17):4764-74 (2012).

Cervantes, A. et al., Pharmacokinetic (PK) and pharmacodynamic (PD) results from 2 phase 1 studies of the investigational selective Aurora A kinase (AAK) inhibitor MLN8237: Exposure-dependent AAK inhibition in human tumors, American Society of Clinical Oncology, poster, (2010).

Cervantes, A. et al., Phase 1 Pharmacokinetic and Pharmacodynamic Study of MLN8237, a Novel, Selective Aurora A Kinase Inhibitor, in Patients with Advanced Solid Tumors, American Society of Clinical Oncology, abstract and poster, 6 pages, (2009).

Chiattone, C. et al., MLN8237 (alisertib), an investigational selective inhibitor of aurora a kinase, versus investigators choice of pralatrexate or gemcitabine in patients with relapsed/refractory peripheral T-cell lymphoma: a phase 3 study, Rev. Bras. Hematol. Hemoter., 34(Supl. 2) 89-326: 300-301(2012).

Dees, C.E. et al., Phase 1 study of the investigational drug MLN8237, an oral Aurora A kinase inhibitor, in patients with solid tumors, Presented at the American Society of Clinical Oncology Annual Meeting, Chicago, Illinois, Jun. 4-8, 2010, 17 pages, (2010).

Dees, E.C. et al., Phase I evaluation of MLN 8237, a novel Aurora A kinase inhibitor, Current Medicine Group, Abstract from Chemotherapy Foundation Symposium XXVI November 116-117 (2008).

Dees, E.C. et al., Phase I study of aurora A kinase inhibitor MLN8237 in advanced solid tumors: safety, pharmacokinetics, pharmacodynamics, and bioavailability of two oral formulations, Clin. Cancer Res., 18(17):4775-84 (2012).

Development Pipeline Presentations: Abstract Compendium, American Society of Clinical Oncology, 18 pages, (2013).

Ditchfield, C. et al., Aurora B couples chromosome alignment with anaphase by targeting BubR1, Mad2, and Cenp-E to kinetochores, Journal of Cell Biology, 161(2):267-280 (2003).

Ecsedy, J. et al., Pharmacokinetics (PK), pharmacodynamics (PD) and exposure-PD relationships of the investigational drug MLN8237, an aurora A kinase inhibitor in patients with advanced solid tumors, Clinical Pharmacology & Therapeutics, 89 (Suppl. 1) S67 (2011).

Extended European Search Report for EP15155821, 4 pages (dated Sep. 4, 2015).

Falchook, G.S. et al., Food effect study of the investigational Aurora A kinase (AAK) inhibitor MLN8237 (alisertib) in patients with advanced solid tumors, European Society for Medical Oncology (ESMO), Annual Congress, Poster (Sep. 28-Oct. 2, 2012).

Friedberg, J. W. et al., Phase II Study of Alisertib, a Selective Aurora A Kinase Inhibitor, in Relapsed and Refractory Aggressive B- and T-Cell Non-Hodgkin Lymphomas, J. Clin. Oncol., 32(1): 44-50 (2014).

Friedberg, J.W. et al., Multicenter Phase 2 Trial of alisertib (MLN8237), an Investigational Inhibitor of Aurora A Kinase, in Patients with Aggressive B-cell and T-cell NHL, American Society of Clinical Oncology, powerpoint, 29 pages (2011).

Goldberg, S.L. et al., Phase 2 study of MLN8237, an investigational Aurora A Kinase inhibitor in patients with acute myelogenous leukemia or myelodysplastic syndromes, The American Society of Hematology, 52nd ASH Annual Meeting in Orlando, Florida, Poster (Dec. 4-7, 2010).

Görgün, G. et al., A Novel Aurora A Kinase Inhibitor MLN8237 Induces Cytotoxicity and Cell Cycle Arrest In Multiple Myeloma, presented at the 51st ASH Annual Meeting and Exposition, Dec. 5-8, 2009, New Orleans, Louisiana, Abstract: 3830, 2 pages (2009).

Görgün, G. et al., A novel Aurora-A kinase inhibitor MLN8237 induces cytotoxicity and cell-cycle arrest in multiple myeloma, Lymphoid Neoplasia: Blood, 115(25):5202-5213 (Jun. 24, 2010).

Green, M. R. et al., Update on Aurora Kinase Targeted Therapeutics in Oncology, Recent Pat. Anticancer Drug Discov., 3(3): 162-177 (2008).

Harrington, E.A. et al., VX-680, a potent and selective small-molecular inhibitor of the Aurora kinases, suppresses tumor growth in vivo, Nature Medicine, 10(3):262-267 (2004).

Hartmann, J. T. and Lipp, H-P, Toxicity of platinum compounds, Expert Opinion on Pharmacotherapy, 4(6): 889-901 (2003).

Hauf, S. et al., The small molecule Hesperadin reveals a role for Aurora B in correcting kinetochore-microtubule attachment and in maintaining the spindle assembly checkpoint, The Journal of Cell Biology, 161(2):281-294 (2003).

Huck, J.J. et al., Antitumor Activity of the Aurora A Inhibitor MLN8237 Combination with Docetaxel in Xenograft Models of Breast and Prostate Cancer, American Association for Cancer Research, 1 (2009).

Infante, J. et al. Phase I study of the safety, pharmacokinetics (PK), and pharmacodynamics (PD) of MLN8237, a selective Aurora A kinase inhibitor, in the United States, presented at the 20th EORTC-NCI-AACR Symposium on Molecular Targets and Cancer Therapeutics in Geneva, Switzerland, Oct. 21-24, 2008, Abstract 279, (2008).

International Search Report for PCT/US2005/016445, 4 pages (dated Dec. 7, 2005).

(56) References Cited

OTHER PUBLICATIONS

International Search Report for PCT/US2007/023948, 6 pages (dated May 8, 2008).
International Search Report for PCT/US2016/043041 (Administration of Aurora Kinase Inhibitor and Chemotherapeutic Agents, filed Jul. 20, 2016), issued by the ISA/US, 3 pages (dated Oct. 4, 2016).
Kelly, K.R. et al., Results from a phase 1 multicenter trial of alisertib (MLN8237)—an investigational Aurora A kinase inhibitor—in patients with advanced hematologic malignancies, 53rd ASH Annual Meeting and Exposition in San Diego, California, Poster (Dec. 10-13, 2011).
Kim, W.S. et al., Phase I Study of MLN9237 (Alisertib) in Adult East Asian Patients (pts) with Advanced Solid Tumors or Lymphomas, Presented at the Palliative care to the geratric oncology patient: An ASCO-NCI-MECC-OCA international Conference in Muscat, Sultanate of Oman, Feb. 10-13, 2013, 24(Suppl 7): Abstract 02-027 (2013).
Kollareddy, M. et al., Aurora kinase inhibitors: Progress towards the clinic, Springer: Invest New Drugs, 30:2411-2432 (2012).
Lee, P., et al. Phase 1/2 study of the investigational Aurora A Kinase (AAK) inhibitor MLN8237 (alisertib) in patients (pts) with non-small cell lung cancer (NSCLC), small cell lung cancer (SCLC), breast cancer (BrC), head/neck cancer (H&N), and gastroesophageal (GE) adenocarcinoma: Preliminary phase 2 results, ASCO 48th Annual Meeting in Chicago, Illinois, Abstract 3010 (Jun. 1-5, 2012).
Li, Q. et al., Development Origins of Irritable Bowel Syndrome (IBS)-Like Symptoms: Epigenetic Dysregulation, Gastroenterology, 140(5): S-121 (2011).
Lu, Y. et al., Knocking down the expression of Aurora-A gene inhibits cell proliferation and induces G2/M phase arrest in human small cell lung cancer cells, Oncology Reports, 32(1):243-249 (2014).
Mahadevan, D. et al., Clinical and Laboratory Evaluation of MLN8237, and Investigational Aurora A Kinase (AAK) Inhibitor, for Treatment of Aggressive Non-Hodgkin's Lymphoma, The Arizona Cancer Center, Peripheral T-cell Lymphomas Symposium, 1 page (2011).
Mahadevan, D. et al., Targeting Aurora Kinase in Aggressive B-Cell Non-Hodgkin's Lymphomas, The American Society of Hematology, 284:1-2 (2009), <https://ash.confex.com/ash/2009/webprogram/Paper20630.html>. Accessed Jun. 29, 2012.
Manfredi, M. G. et al., Antitumor activity of MLN8054, an orally active small-molecule inhibitor of Aurora A kinase, PNAS, 104(10): 4106-4111 (2007).
Matulonis, U.A. et al., Phase II study of MLN8237 (alisertib), an investigational Aurora A kinase inhibitor, in patients with platinum-resistant or -refractory epithelial ovarian, fallopian tube, or primary peritoneal carcinoma. Gynecol Oncol., 127(1):63-9 (2012).
Matulonis, U.A. et al., Single-agent activity and safety of teh investigational Aurora A kinase inhibitor MLN8237 in patients with platinum-treated epithelial ovarian, fallopian tube, or primary peritoneal carcinoma, American Society of Clinical Oncology, 35th ESMO Congress in Milan, Italy, Poster (Oct. 8-12, 2010).
Melichar, B. et al., MLN8237 (alisertib), an investigational Aurora A kinase inhibitor, in patients with non-small cell lung cancer, small cell lung cancer, breast cancer, head and neck squamous cell carcinoma, and gastroesophageal cancer: Emerging phase 2 results, American Society of Clinical Oncology, European Society for Medical Oncology (ESMO) Annual Congress in Vienna, Austria, Poster, (Sep. 28-Oct. 2, 2012).
Melichar, B. et al., Phase 1/2 study of investigational Aurora A Kinase inhibitor MLN8237 (alisertib): Updated phase 2 results in patients with small lung cancer (SCLC), non-SCLC (NSCLC), breast cancer (BrC), head and neck squamous cell carcinoma (HNSCC), and gastroesophageal cancer (GE), American Society of Clinical Oncology, abstract and poster, 4 pages, (2013).
Meraldi, P. et al., Aurora-A overexpression reveals tetraploidization as a major route to centrosome amplification in p53$^{-/-}$ cells, The European Molecular Biology Organization Journal, 21(4):483-492 (2002).

Mossé, Y. P. et al., Pediatric Phase I Trial and Pharmacokinetic Study of MLN8237, an Investigational Oral Selective Small-Molecule Inhibitor of Aurora Kinase A: A Children's Oncology Group Phase I Consortium Study, Clinical Cancer Res., 18(21): 6058-6064 (2012).
Mosse, Y.P. et al., Pediatric Phase 1 Trial and Pharmacokinetic Study of MLN8237, an Oral Selective Small Molecule Inhibitor of Aurora A Kinase: A Children's Oncology Group Phase 1 Consortium Study, American Society of Clinical Oncology, poster, (2010).
Nawrocki, S.T. et al., The Aurora Kinase Inhibitor MLN8237 has Potent Anticancer Activity in CML and Ph$_+$ALL Models and Significantly Increases the Efficacy of Nilotinib, Blood, 112:1-2 (2008).
O'connor, O.A. et al., Phase 3 Study of investigational MLN8237 vs. investigator's choice in patients with relapsed/refractory peripheral t-cell lymphoma, American Society of Clinical Oncology, 2012 ASCO Annual Meeting Proceedings in Chicago, Illinois, Abstract TPSB110 and Poster, 7 pages (Jun. 1-5, 2012).
Padmanabhan, S. et al., Phase I Study of an Investigational Aurora A Kinase Inhibitor MLN8237 in Patients with Advanced Hematologic Malignancies, Blood Journal of the American Society of Hematology, presented at the 52nd Annual Meeting in Orlando, Florida, Dec. 4-7, 2010, Abstract 2799, (2010).
Padmanabhan, S. et al., Phase I Study of an investigational Aurora A Kinase inhibitor MLN8237 in patients with advanced hematologic malignancies, American Society of Clinical Oncology, Presented at the 52nd ASH Annual Meeting, Dec. 4-7, 2010, Orlando, FL, USA, Poster (2010).
Sausville, E.A., Aurora kinases dawn as cancer drug targets, Nature Medicine, 10(3):234-235 (2004).
Sehdev, V. et al., MLN-8237 Treatment Alone and in Combination with Cisplatin Supresses In Vitro and In Vivo Progression of Gastrointestinal Cancer Cells, Gastroenterology, 140(5):Supplemental 1, S121 (2011), Presented at Digestive Disease Week in Chicago, IL, USA, May 7-10, 2011.
Sehdev, V. et al., The Aurora Kinase A Inhibitor MLN8237 Enhances Cisplatin-Induced Cell Death in Esophageal Adenocarcinoma Cells, Molecular Cancer Therapeutics, 11(3): 763-744 (2012).
Sharma, S. et al., Phase 1 dose-escalation study of the investigational Aurora A Kinase Inhibitor MLN8237 as an enteric-coated tablet formulation in patients with non-hematologic malignancies, American Society of Clinical Oncology, Annual Meeting of the American Society of Clinical Oncology in Chicago, Illinois, Poster (Jun. 3-7, 2011).
Shokakiegka Nursing, Digestive Surgery Nursing, 17(9):891-897 (2012). [Japanese].
Solowey, W.E. et al., Peripheral-Acting Benzodiazepines Inhibit the Growth of Human Melanoma Cells and Potentiate the Antiproliferative Activity of Recombinant Human Interferons, The Journal of Interferon Research, 10(3):269-280 (1990).
Tabernero, C.J. et al., MLN8237, an oral selective Aurora A kinase inhibitor: initial results of dose-finding pharmacokinetic-pharmacodynamic phase I study, Eur. J. Cancer, 6:(92 Suppl) (2008).
Third Party Opposition against CR 2014-0544, 7 pages (Apr. 24, 2015). [English translation, 8 pages].
Vankayalapati, H. et al., Targeting Aurora2 Kinase in Oncogenesis: A Structural Bioinformatics Approach to Target Validation and Rational Drug Design, Molecular Cancer Therapeutics, 2:283-294 (2003).
Venkatakrishnan, K. et al., Clinical pharmacologic considerations for the phase 2/3 dose/regimen of the investigational Aurora A kinase inhibitor MLN8237 (alisertib): Pharmacokinetics, pharmacodynamics, and exposure-safety relationships, American Society of Clinical Oncology, Presented at the 48th Annual Meeting of the American Society of Clinical Oncology, Jun. 4, 2012, Chicago, IL, USA, Poster of Abstract 2597 (2012).
Wang, J.K.T. et al., Benzodiazepines that bind at peripheral sites inhibit cell proliferation, Proceedings of the National Academy of Sciences, 81:753-756 (1984).
Written Opinion for PCT/US2005/016445, 6 pages (dated Dec. 7, 2005).

(56) References Cited

OTHER PUBLICATIONS

Written Opinion for PCT/US2007/023948, 9 pages (dated May 8, 2008).

Written Opinion for PCT/US2016/043041 (Administration of Aurora Kinase Inhibitor and Chemotherapeutic Agents, filed Jul. 20, 2016), issued by ISA/US, 4 pages (dated Oct. 4, 2016).

Xia, W. et al., Tumor selective G2/M cell cycle arrest and apoptosis of epithelial and hematological malignancies by BBL22, a benzazepine, Proceedings of the National Academy of Sciences, 97(13):7494-7499 (2000).

Xu, J. et al., Aurora-A contributes to cisplatin resistance and lymphatic metastasis in non-small cell lung cancer and predicts poor prognosis, Journal of Translational Medicine, 12: 200, 14 pages (2014).

Zhang, M. et al., Aurora A Kinase Inhibitor MLN8237 in Combination with Docetaxel Induces Synergistic Antitumor Activity in Triple-Negative Breast Cancer Xenograft Models, Presented at the 22nd EORTC—NCI-AACR Symposium, Nov. 15-19, 2010, Berlin, Germany, poster, (2010).

Zhou, H. et al., Tumor amplified kinase *STK15/BTAK* induces centrosome amplification, aneuploidy and transformation, Nature Genetics, 20:189-193 (1998).

\* cited by examiner

Figure 1: Evaluating the anti-tumor activity of alisertib and carboplatin in the NCI-H82 xenograft model Figure 2: Evaluating the anti-tumor activity of alisertib and cisplatin in the NCI-H82 xenograft model Figure 3: Evaluating the anti-tumor activity of alisertib and cisplatin in the NCI-H69 xenograft model

ADMINISTRATION OF AURORA KINASE INHIBITOR AND CHEMOTHERAPEUTIC AGENTS

PRIORITY

This application claims the benefit of U.S. Provisional Patent Application No. 62/195,103, filed Jul. 21, 2015, which is incorporated by reference in their entirety.

FIELD

This present disclosure relates to oncology and to methods for the treatment of cancer. In particular, the present disclosure provides methods for treatment of various cancers by administering an Aurora kinase inhibitor in combination with one or more chemotherapeutic agents.

BACKGROUND

Cancer is the second most common cause of death in the U.S. and accounts for one of every eight deaths globally (American Cancer Society, Cancer Facts and Figures, 2014). The American Cancer Society expects that in 2014 at least 1,665,540 new cancer cases will be diagnosed in the US and 585,720 Americans are expected to die of cancer, almost 1,600 people per day. Currently available paradigms for treating solid tumors may include systemic treatment such as chemotherapy, hormonal therapy, use of targeted agents and biological agents, either as single agents or in combination. These treatments can be delivered in combination with localized treatments such as surgery or radiotherapy. These anti-cancer paradigms can be use in the curative setting as adjuvant or neo-adjuvant treatments or in the metastatic setting as palliative case for prolonged survival and to help manage symptoms and side-effects. In hematological cancers, stem cell transplants may also be an option in certain cancers as well as chemotherapy and/or radiation. Although medical advances have improved cancer survival rates, there remains a continuing need for new and more effective treatments.

Cancer is characterized by uncontrolled cell reproduction. Uncontrolled cell reproduction results from the deregulation of the normal processes that control cell division, differentiation and apoptotic cell death. Mitosis is a stage in the cell cycle during which a series of complex events ensure the fidelity of chromosome separation into two daughter cells. Mitotic progression is largely regulated by proteolysis and by phosphorylation events that are mediated by mitotic kinases. Aurora kinase family members (e.g., Aurora A, Aurora B) regulate mitotic progression through modulation of centrosome separation, spindle dynamics, spindle assembly checkpoint, chromosome alignment/segregation, and cytokinesis. Overexpression and/or amplification of Aurora kinases have been linked to oncogenesis in several tumor types including those of colon and breast. Moreover, Aurora kinase inhibition in tumor cells results in mitotic arrest and apoptosis, suggesting that these kinases are important targets for cancer therapy.

New combinations of therapeutic agents that provide a beneficial effect in the treatment of cancers are desirable in order to prolong patient's lives while maintaining a high quality of life. Further, new combinations may provide an increased benefit as compared to each of the agents alone. This is especially true in the case where the cancers may be resistant or refractory to currently available therapeutic regimens.

SUMMARY

In one aspect, the present disclosure relates to methods of treating cancer comprising administering an Aurora kinase inhibitor and a platin in combination to a patient in need of such treatment.

In some embodiments, the Aurora kinase inhibitor is 4-{[9-chloro-7-(2-fluoro-6-methoxyphenyl)-5H-pyrimido[5,4-d][2]benzazepin-2-yl]amino}-2-methoxybenzoic acid (alisertib (MLN8237)) of formula (I), or a pharmaceutically acceptable salt thereof:

(I)

In some embodiments, the Aurora kinase inhibitor is sodium 4-{[9-chloro-7-(2-fluoro-6-methoxyphenyl)-5H-pyrimido[5,4-d][2]benzazepin-2-yl]amino}-2-methoxybenzoate of formula (II), or a crystalline form thereof:

(II)

In one aspect, the present disclosure relates to methods of treating cancer comprising administering 4-{[9-chloro-7-(2-fluoro-6-methoxyphenyl)-5H-pyrimido[5,4-d][2]benzazepin-2-yl]amino}-2-methoxybenzoic acid or a pharmaceutically acceptable salt thereof and a platin in combination to a patient in need of such treatment, wherein the cancer is breast cancer, small cell lung cancer, or gastric cancer.

In one aspect, the present disclosure relates to a kit comprising a medicament for use in treating cancer in a subject in need of such treatment. The kit comprises a medicament comprising an Aurora kinase inhibitor, and instructions for administering the Aurora kinase inhibitor and a platin; or the kit comprises a medicament comprising a platin, and instructions for administering the platin and an Aurora kinase inhibitor. The kit can contain both a medicament comprising an Aurora kinase inhibitor and a medicament comprising a platin, and instructions for administering the Aurora kinase inhibitor and the platin.

In one aspect, the present disclosure relates to a medicament for use in treating cancer in a subject in need of such treatment. The medicament comprises an Aurora kinase inhibitor and a platin.

DESCRIPTION

Definitions and Abbreviations

AUC area under the plasma concentration versus time curve
BSA body surface area
CR complete response
MTD maximum tolerated dose
IV Intravenous(ly)
IP Intraperitoneal(ly)
PR partial response
BIW twice weekly
QD once daily
Q every
NSCLC non-small cell lung cancer
SCLC small cell lung cancer As used herein, the term "cancer" refers to a cellular disorder characterized by uncontrolled or dysregulated cell proliferation, decreased cellular differentiation, inappropriate ability to invade surrounding tissue, and/or ability to establish new growth at ectopic sites. The term "cancer" includes solid tumors and hematological tumors. The term "cancer" encompasses diseases of skin, tissues, organs, bone, cartilage, blood, and vessels. The term "cancer" further encompasses primary and metastatic cancers.

As used herein, "clinically effective amount" means an amount of a therapeutic substance that is sufficient upon appropriate administration to a patient (a) to cause a detectable decrease in the severity of the disorder or disease state being treated; (b) to ameliorate or alleviate the patient's symptoms of the disease or disorder; or (c) to slow or prevent advancement of, or otherwise stabilize or prolong stabilization of, the disorder or disease state being treated (e.g., prevent additional tumor growth of a cancer).

When more than one therapeutic substance is being administered, the "clinically effective total amount" means that the sum of the individual amounts of each therapeutic substance meets the definition of "clinically effective amount" even if the individual amounts of any number of the individual therapeutic substances would not. For example, if 10 mg of A were not a clinically effective amount, and 20 mg of B were not a clinically effective amount, but the administration of 10 mg A+20 mg B resulted in at least one of the results enumerated for the definition of "clinically effective amount" then the sum of 10 mg A+20 mg B would be considered a "clinically effective total amount".

In any form or composition, the administered dose(s) or the clinically effective (total) amount can be expressed as amount(s) of therapeutic substance(s) per patient as either based on (i) BSA, e.g., as mg/m$^2$, or (ii) amount e.g. as mg.

As used herein, "patient" means a human being diagnosed with, exhibiting symptoms of or otherwise believed to be afflicted with a disease, disorder or condition.

As used herein, "body surface area" (BSA) is calculated using a standard nomogram, e.g., $$BSA\ (m^2) = \sqrt{\frac{Ht\ (cm) \times Wt\ (kg)}{3600}}\ \text{or}\ BSA = \sqrt{\frac{Ht\ (in) \times Wt\ (lb)}{3131}}$$

As used herein, dosing for carboplatin is based upon an estimate of the GFR (glomerular filtration rate) and the desired level of drug exposure, according to the area under the curve of concentration X time (AUC, mg/mL×min), rather than the more common dosing calculation based upon the body surface area (mg/m$^2$). For a desired target AUC (which typically varies between 5 and 7 mg/mL×min) and the estimated GFR, the dose of carboplatin is then calculated by use of the Calvert formula:

Total carboplatin dose, mg=Target AUC×(estimated creatinine clearance+25).

Because of potential changes in weight or renal function, this calculation should be repeated prior to each administered course of carboplatin.

The estimation of the GFR is based upon a calculation of creatinine clearance according to the Cockcroft-Gault Equation (Cockcroft D W, Gault M H. Prediction of creatinine clearance from scrum creatinine. Nephron. 1976; 16(1):31-41):

For males:

Creatinine Clearance=(140−age [years]×weight [kg])/72×(serum creatinine [mg/dL])

For females:

Creatinine Clearance=0.85(140−age [years]×weight [kg])/72×(serum creatinine [mg/dL]).

As used herein, the illustrative terms "include", "such as", "for example" and the like (and variations thereof, e.g., "includes" and "including", "examples"), unless otherwise specified, are intended to be non-limiting. That is, unless explicitly stated otherwise, such terms are intended to imply "but not limited to", e.g., "including" means including but not limited to.

Unless otherwise stated, structures depicted herein are meant to include chemical entities which differ only in the presence of one or more isotopically enriched atoms. For example, chemical entities having the present structure except for the replacement of a hydrogen atom by a deuterium or tritium, or the replacement of a carbon atom by a $^{13}C$- or $^{14}C$-enriched carbon are within the scope of the invention.

Unless stereochemical configuration is denoted, structures depicted herein are meant to include all stereochemical forms of the structure, i.e., the R and S configurations for each asymmetric center. Therefore, unless otherwise indicated, single stereochemical isomers as well as enantiomeric, racemic and diastereomeric mixtures of the present chemical entities are within the scope of the invention. When a stereochemical configuration is denoted for a compound, the diastereoisomeric or enantiomeric excess of the compound is at least 99.0%, 99.5%, 99.6%, 99.7%, 99.8% or 99.9%.

DETAILED DESCRIPTION

In some embodiments, the present disclosure relates to a method of treating cancer in a patient by administering to a patient a combination of an Aurora kinase inhibitor or pharmaceutically acceptable salt thereof and a platin.

In some embodiments, the present disclosure relates to a method of treating cancer in a patient by administering to a patient a combination of an Aurora kinase inhibitor or pharmaceutically acceptable salt thereof and a platin, wherein the cancer is breast cancer, small cell lung cancer, or gastric cancer.

Compounds capable of inhibiting the enzymatic activity of an Aurora kinase may be used in the methods of the instant disclosure. In particular, Aurora kinase inhibitors include the compounds described herein, as well as compounds disclosed in, for example, WO 05/111039, US 2005/0256102, US 2007/185087, WO 08/021038, US 2008/0045501, WO 08/063525, US 2008/0167292, WO 07/113212, EP 1644376, US 2005/0032839, WO 05/005427, WO 06/070192, WO 06/070198, WO 06/070202, WO 06/070195, WO 06/003440, WO 05/002576, WO 05/002552, WO 04/071507, WO 04/058781, WO 06/055528, WO 06/055561, WO 05/118544, WO 05/013996, WO 06/036266, US2006/0160874, US2007/0142368, WO 04/043953, WO 07/132220, WO 07/132221, WO 07/132228, WO 04/00833 and WO 07/056164. Also suitable for use in the methods of the disclosure are solvated and hydrated forms of any of these compounds. Also suitable for use in the methods of the disclosure are pharmaceutically acceptable salts of any of the compounds, and solvated and hydrated forms of such salts. These Aurora kinase inhibitors can be prepared in a number of ways well known to one skilled in the art of organic synthesis, including, but not limited to, the methods of synthesis described in detail in the above references.

In some embodiments the Aurora kinase inhibitor is a small molecular weight compound. In particular, the Aurora kinase inhibitor include the compounds described herein, as well as compounds disclosed in, for example, US 2008/0045501, U.S. Pat. No. 7,572,784, WO 05/111039, WO 08/021038, U.S. Pat. No. 7,718,648, WO 08/063525, US 2008/0167292, U.S. Pat. No. 8,026,246, WO 10/134965, US 2010/0310651, WO 11/014248, US 2011/0039826, and US 2011/0245234, each of which is hereby incorporated by reference in its entirety, sodium 4-{[9-chloro-7-(2-fluoro-6-methoxyphenyl)-5H-pyrimido[5,4-d][2]benzazepin-2-yl]amino}-2-methoxybenzoate, KW-2449 (Kyowa), ENMD-2076 (EntreMed), and MK-5108 (Vertex/Merck). In some embodiments the Aurora kinase inhibitor is an Aurora A kinase inhibitor.

Aurora A kinase inhibitors can be assayed in vitro or in vivo for their ability to selectively bind to and/or inhibit an Aurora A kinase. In vitro assays include assays to determine selective inhibition of the ability of an Aurora A kinase to phosphorylate a substrate protein or peptide. Alternate in vitro assays quantitate the ability of the compound to selectively bind to an Aurora A kinase. Selective inhibitor binding may be measured by radiolabelling the inhibitor prior to binding, isolating the inhibitor/Aurora A kinase complex and determining the amount of radiolabel bound. Alternatively, selective inhibitor binding may be determined by running a competition experiment in which new inhibitors are incubated with Aurora A kinase bound to a known radioligand. The compounds also can be assayed for their ability to affect cellular or physiological functions mediated by Aurora A kinase activity. In order to assess selectivity for Aurora A kinase over Aurora B kinase, inhibitors can also be assayed in vitro and in vivo for their ability to selectively bind to and/or inhibit an Aurora B kinase, using assays analogous to those described above for Aurora A kinase.

Inhibitors can be assayed in vitro and in vivo for their ability to inhibit Aurora A kinase in the absence of Aurora B kinase inhibition, by immunofluorescent detection of pHisH3. (*Proc. Natl. Acad. Sci.* (2007) 104, 4106). Assays for each of these activities are known in the art.

In some embodiments, the Aurora kinase inhibitor is 4-{[9-chloro-7-(2-fluoro-6-methoxyphenyl)-5H-pyrimido[5,4-d][2]benzazepin-2-yl]amino}-2-methoxybenzoic acid (alisertib (MLN8237)) of formula (I), or a pharmaceutically acceptable salt thereof:

(I)

In some embodiments, a pharmaceutically acceptable salt of formula (I) is sodium 4-{[9-chloro-7-(2-fluoro-6-methoxyphenyl)-5H-pyrimido[5,4-d][2]benzazepin-2-yl]amino}-2-methoxybenzoate of formula (II), or a crystalline form thereof:

(II)

In some embodiments, the compound of formula (II) is sodium 4-{[9-chloro-7-(2-fluoro-6-methoxyphenyl)-5H-pyrimido[5,4-d][2]benzazepin-2-yl]amino}-2-methoxybenzoate. In some embodiments, the compound of formula (II) is sodium 4-{[9-chloro-7-(2-fluoro-6-methoxyphenyl)-5H-pyrimido[5,4-d][2]benzazepin-2-yl]amino}-2-methoxybenzoate monohydrate. In some embodiments, the compound of formula (II) is sodium 4-{[9-chloro-7-(2-fluoro-6-methoxyphenyl)-5H-pyrimido[5,4-d][2]benzazepin-2-yl]amino}-2-methoxybenzoate polymorph Form 2, as described in US2008/0167292, U.S. Pat. No. 8,026,246, and US 2011/0245234, each of which is hereby incorporated by reference in their entirety.

Platinum containing chemotherapeutic agents ("platins") include agents such as cisplatin, carboplatin, oxaliplatin, satraplatin, picoplatin, nedaplatin and triplatin. Platinum containing chemotherapeutic agents cause crosslinking of DNA as monoadduct, interstrand crosslinks, intrastrand crosslinks or DNA protein crosslinks. The resulting crosslinking inhibits DNA repair and/or DNA synthesis in cancer cells. These agents are sometimes described as being alkylating-like agents despite the fact that they do not have an alkyl group. Cisplatin was the first platinum containing compound to be discovered and was first approved by the U.S. Food and Drug Administration in 1978. Carboplatin was introduced in the 1980s and has been demonstrated to have lower side-effects than cisplatin in ovarian cancer and lung cancer (Hartmann and Lipp, *Exper. Opin. Pharmacother.* 2003, 4(6) 889-901).

In some embodiments, the platin is cisplatin, carboplatin, oxaliplatin, satraplatin, picoplatin, nedaplatin or triplatin. In some embodiments, the platin is nedaplatin, cisplatin, carboplatin or oxaliplatin. In some embodiments, the platin is cisplatin, carboplatin or oxaliplatin. In some embodiments, the platin is cisplatin or carboplatin. In some embodiments, the platin is cisplatin. In some embodiments, the platin is carboplatin.

In some embodiments, the present disclosure relates to a method of treating cancer in a patient by administering to a patient a combination of alisertib or pharmaceutically acceptable salt thereof and a platin.

In another aspect, the present disclosure relates to the use of alisertib or a pharmaceutically acceptable salt in combination with a platin for the treatment of cancer.

In another aspect, the present disclosure relates to the use of alisertib or a pharmaceutically acceptable salt in combination with a platin in the manufacture of a medicament for use in treating cancer.

In another aspect, the present disclosure relates to the use of alisertib or a pharmaceutically acceptable salt in the manufacture of a medicament for treating cancer, wherein alisertib or a pharmaceutically acceptable salt thereof is administered with a platin.

In another aspect, the present disclosure relates to a kit for treating cancer comprising at least one medicament comprising at least one dose of alisertib or a pharmaceutically acceptable salt thereof, and at least one medicament comprising at least one dose of a platin, said kit for treating cancer further comprising dosing instructions for administering the medicaments for treatment of the subject in recognized need thereof.

Alisertib or a pharmaceutically acceptable salt thereof can be administered in combination with the platin in a single dosage form or as a separate dosage forms. In one embodiment, when administered as a separate dosage form, the platin can be administered prior to, at the same time as, or following administration of alisertib. In some embodiments, when administered as a separate dosage form, one or more doses of alisertib or a pharmaceutically acceptable salt thereof, may be administered prior to the platin. In some embodiments, the platin is administered prior to the administration of alisertib or a pharmaceutically acceptable salt thereof. As used herein, the administration in "combination" of alisertib and a platin refers not only to simultaneous or sequential administration of the two agents, but also to the administration of both compounds during a single treatment cycle, as understood by one skilled in the art. When alisertib or a pharmaceutically acceptable salt thereof is administered in combination with the platin a clinically effective total amount is administered.

The Aurora kinase inhibitor can be administered by any method known to one skilled in the art. For example, the Aurora kinase inhibitor can be administered in the form of a second composition, in some embodiments a pharmaceutical composition of the Aurora kinase inhibitor and a pharmaceutically acceptable carrier, such as those described herein. In one aspect, the pharmaceutical composition is suitable for oral administration. In some embodiments, the pharmaceutical composition is a tablet for oral administration, such as an enteric coated tablet. Such tablets are described in US 2010/0310651, which is hereby incorporated by reference in its entirety. In some other embodiments, the pharmaceutical composition is a liquid dosage form for oral administration. Such liquid dosage forms are described in US 2011/0039826, hereby incorporated by reference. In some embodiments, these compositions optionally further comprise one or more additional therapeutic agents.

In some embodiments, the platin is administered intravenously (IV).

In some embodiments, the present disclosure relates to a method of treating cancer in a patient by administering to a patient a combination of alisertib or pharmaceutically acceptable salt thereof, a platin, and a further therapeutic agent.

In some embodiments, the further therapeutic agent is a taxane. Taxanes are diterpenes produced by the plants of the genus *Taxus* (yew trees). Taxanes were first discovered and isolated from this natural source but are mostly now produced by synthetic or semi-synthetic methods. The principle mechanism by which taxanes exert their effect is the disruption of microtubule function during cell division, thereby preventing effective growth and division of cancer cells. Taxane agents include paclitaxel, docetaxel and nab-paclitaxel. In some embodiments, the taxane is paclitaxel. In some embodiments, the taxane is docetaxel.

In some embodiments, the present disclosure relates to a method of treating cancer in a patient by administering to a patient a combination of alisertib or pharmaceutically acceptable salt thereof, a platin, and paclitaxel. In some embodiments, the present disclosure relates to a method of treating cancer in a patient by administering to a patient a combination of alisertib or pharmaceutically acceptable salt thereof, a platin, and a docetaxel.

In some embodiments, the cancer is a solid tumor. Non-limiting examples of solid tumors include pancreatic cancer; bladder cancer, including invasive bladder cancer; colorectal cancer; thyroid cancer; gastric cancer; breast cancer, including metastatic breast cancer; prostate cancer, including androgen-dependent and androgen-independent prostate cancer; renal cancer, including, e.g., metastatic renal cell carcinoma; liver cancer including e.g. hepatocellular cancer and intrahepatic bile duct; lung and bronchus cancer including non-small cell lung cancer (NSCLC), squamous lung cancer, brochioloalveolar carcinoma (BAC), adenocarcinoma of the lung, and small cell lung cancer (SCLC); ovarian cancer including, e.g., progressive epithelial and primary peritoneal cancer; cervical cancer; uterine cancer including e.g. uterine corpus and uterine cervix; endometrial cancer; esophageal cancer; head and neck cancer, including, e.g., squamous cell carcinoma of the head and neck, nasopharyngeal cancer, oral cavity and pharynx; melanoma; neuroendocrine cancer, including metastatic neuroendocrine tumors; brain cancer, including, e.g., glioma/glioblastoma, anaplastic oligodendroglioma, adult glioblastoma multiforme, and adult anaplastic astrocytoma; neuroendocrine cancer, including metastatic neuroendocrine tumors; bone cancer; gastro-esophageal junction cancer, and soft tissue sarcoma.

In some embodiments, the cancer is breast cancer, colorectal cancer, ovarian cancer, lung cancer, prostate cancer, gastric cancer, or head and neck cancer. In some embodiments, the cancer is breast cancer, colorectal cancer, ovarian cancer, gastric cancer, or lung cancer. In some embodiments, the cancer is breast cancer, gastric cancer, or small cell lung cancer. In some embodiments, the cancer is gastric cancer, or small cell lung cancer.

In some embodiments, the cancer is lung cancer. Lung cancer includes different sub-types such as small cell lung cancer (SCLC); non-small cell lung cancer (NSCLC) including squamous NSCLC; bronchioloalveolar carcinoma (BAC); and adenocarcinoma. In some embodiments, the cancer is small cell lung cancer. In some embodiments, the cancer is non-small cell lung cancer.

In some embodiments, the cancer is breast cancer. Breast cancer includes different sub-types such as luminal A, luminal B, triple-negative (basal-like) and HER-2 type. In some embodiments, the cancer is triple-negative breast cancer.

In some embodiments, the cancer is ovarian cancer. Ovarian cancer includes different sub-types such as epithelial, germ-cell and sex-cord stromal. Primary peritoneal carcinoma is a related cancer that starts in the lining of the pelvis and abdomen. In some embodiments, the cancer is epithelial ovarian cancer.

In some embodiments, the cancer is prostate cancer. Prostate cancer includes androgen-dependent and androgen independent prostate cancer and adenocarcinomas.

In some embodiments, the cancer is gastric cancer. Adenocarcinoma is the most common type of gastric cancer. Other gastric cancers may include gastrointestinal carcinoid tumors, gastrointestinal stromal tumors, and lymphomas.

In some embodiments, the cancer is esophageal cancer. The most common types of esophageal cancer are squamous cell carcinoma and adenocarcinoma. Gastro-esophageal cancer is a related cancer that develops at the point where the esophagus joins the stomach.

In some embodiments, the cancer is colorectal cancer. Adenocarcinoma is the most common type of colorectal cancer. Other colorectal cancers may include gastrointestinal carcinoid tumors, gastrointestinal stromal tumors, and squamous cell carcinoma.

In some embodiments, the cancer is head and neck cancer. Head and neck cancer are those that arise in the head and neck region and the cancer may be found in areas such as nasal cavities, sinuses, lips, mouth, salivary glands, pharynx or larynx. 90% of head and neck cancers are squamous cell carcinomas (SCCHN), which originate from the mucosal lining (epithelium) of these regions.

In some embodiments, the cancer is a hematological cancer. In some embodiments, the cancer is multiple myeloma, Hodgkin's lymphoma, or non-Hodgkin's lymphoma.

In some embodiments, the cancer is relapsed. In one aspect, relapsed cancer is cancer which has returned after a period of time in which no cancer could be detected.

In some embodiments, the cancer is refractory. In one aspect, refractory cancer does not respond to cancer treatment; it is also known as resistant cancer. In some embodiments, the cancer is resistant to a platin. In some embodiments, the cancer does not respond to the treatment of a platin. In some embodiments, the cancer is platin-resistant recurrent cancer. In some embodiments, the patient has become refractory to a platin-containing regimen. In some embodiments, the tumor is unresectable. In one aspect, an unresectable tumor is unable to be removed by surgery. In some embodiments, the cancer has not been previously treated. In some embodiments, the cancer is locally advanced. In one aspect, "locally advanced" refers to cancer that is somewhat extensive but still confined to one area. In some instances, "locally advanced" can refer to a small tumor that hasn't spread but has invaded nearby organs or tissues that make it difficult to remove with surgery alone. In some embodiments, the cancer is metastatic. In one aspect, metastatic cancer is a cancer that has spread from the part of the body where it started (the primary site) to other parts of the body.

In some embodiments, the cancer is an Aurora kinase-mediated disorder. In some embodiments, the cancer is an Aurora A kinase-mediated disorder.

In some embodiments, alisertib or a pharmaceutically acceptable salt thereof is administered 3 days on and 4 days off for 3 weeks of a 4 week cycle (e.g., 28-days). In some embodiments, alisertib or a pharmaceutically acceptable salt thereof is administered on a 28-day cycle in which alisertib or a pharmaceutically acceptable salt thereof is administered on days 1, 2, 3, 8, 9, 10, 15, 16, and 17 of a 28-day cycle. In some embodiments, alisertib or a pharmaceutically acceptable salt thereof is administered twice-daily on a 28-day cycle in which alisertib or a pharmaceutically acceptable salt thereof is administered on days 1, 2, 3, 8, 9, 10, 15, 16, and 17 of a 28-day cycle.

In some embodiments, suitable daily dosages of alisertib or a pharmaceutically acceptable salt thereof can generally range, in single or divided or multiple doses, from about 20 mg to about 120 mg per day. Other suitable daily dosages of alisertib or a pharmaceutically acceptable salt thereof can generally range, in single or divided or multiple doses, from about 30 mg to about 90 mg per day. Other suitable daily dosages of alisertib or a pharmaceutically acceptable salt thereof can generally range, in single or divided or multiple doses, from about 40 mg to about 80 mg per day.

In some embodiments, the suitable dosages are from about 10 mg to about 50 mg per dose given twice daily. In some embodiments, the suitable dosages are from about 15 mg to about 50 mg per dose given twice daily. In some other embodiments, the suitable dosages are from about 25 mg to about 40 mg per dose given twice daily. In certain other embodiments, suitable dosages are about 10 mg, about 15 mg, about 20 mg, about 25 mg, about 30 mg, about 35 mg, about 40 mg, about 45 mg, about 50 mg, about 55 mg, or about 60 mg per dose given twice daily. In some embodiments, the suitable dosage of alisertib or a pharmaceutically acceptable salt thereof is about 15 mg per dose given twice daily. In some embodiments, the suitable dosage of alisertib or a pharmaceutically acceptable salt thereof is about 20 mg per dose given twice daily. In some embodiments, the suitable dosage of alisertib or a pharmaceutically acceptable salt thereof is about 25 mg per dose given twice daily. In some embodiments, the suitable dosage of alisertib or a pharmaceutically acceptable salt thereof is about 30 mg per dose given twice daily. In some embodiments, the suitable dosage of alisertib or a pharmaceutically acceptable salt thereof is about 35 mg per dose given twice daily. In some embodiments, the suitable dosage of alisertib or a pharmaceutically acceptable salt thereof is about 40 mg per dose given twice daily. In some embodiments, the suitable dosage of alisertib or a pharmaceutically acceptable salt thereof is about 50 mg per dose given twice daily.

In some embodiments, a platin is administered on day 1 of a 21 day schedule. In some embodiments, a platin is administered on day 1 of a 28 day schedule. In some embodiments, a platin is administered on each of days 1, 8, and 15 of a 21 day schedule. In some embodiments, a platin is administered on each of days 1, 8, and 15 of a 28 day schedule.

In some embodiments, carboplatin is administered on day 1 of a 21 day schedule. In some embodiments, the amount of carboplatin that is administered on day 1 of a 21 day schedule is AUC 6 (calculated as per the Calvert calculation above). In some embodiments, the amount of carboplatin that is administered on day 1 of a 21 day schedule is AUC 5.

In some embodiments, carboplatin is administered on day 1 of a 28 day schedule. In some embodiments, the amount of carboplatin that is administered on day 1 of a 28 day schedule is AUC 6 (calculated as per the Calvert calculation above). In some embodiments, the amount of carboplatin that is administered on day 1 of a 28 day schedule is AUC 5.

In some embodiments, carboplatin is administered on each of days 1, 8, and 15 of a 21 day schedule. In some embodiments, the amount of carboplatin that is administered on each of days 1, 8, and 15 of a 21 day schedule is AUC 2-6.

In some embodiments, carboplatin is administered on each of days 1, 8, and 15 of a 28 day schedule. In some embodiments, the amount of carboplatin that is administered on each of days 1, 8, and 15 of a 28 day schedule is AUC 2-6.

In some embodiments, cisplatin is administered on day 1 of a 21 day schedule. In some embodiments, the amount of cisplatin administered on day 1 of a 21 day schedule is about 75 mg/m$^2$ to about 100 mg/m$^2$. In some embodiments, the amount of cisplatin administered on day 1 of a 21 day schedule is about 50 mg/m$^2$ to about 70 mg/m$^2$.

In some embodiments, cisplatin is administered on day 1 of a 28 day schedule. In some embodiments, the amount of cisplatin administered on day 1 of a 28 day schedule is about 75 mg/m$^2$ to about 100 mg/m$^2$. In some embodiments, the amount of cisplatin administered on day 1 of a 28 day schedule is about 50 mg/m$^2$ to about 70 mg/m$^2$.

In some embodiments, cisplatin is administered on each of days 1, 8, and 15 of a 21 day schedule. In some embodiments, the amount of cisplatin that is administered on each of days 1, 8, and 15 of a 21 day schedule is about 25 mg/m$^2$ to about 50 mg/m$^2$.

In some embodiments, cisplatin is administered on each of days 1, 8, and 15 of a 28 day schedule. In some embodiments, the amount of cisplatin that is administered on each of days 1, 8, and 15 of a 28 day schedule is about 25 mg/m$^2$ to about 50 mg/m$^2$.

In some embodiments, alisertib or a pharmaceutically acceptable salt thereof is administered on each of days 1, 2, 3, 8, 9, 10, 15, 16, and 17 of a 28 day schedule, and a platin is administered on day 1 of a 28 day schedule.

In some embodiments, alisertib or a pharmaceutically acceptable salt thereof is administered on each of days 1, 2, 3, 8, 9, 10, 15, 16, and 17 of a 28 day schedule, and a platin is administered on each of days 1, 8, and 15 of a 28 day schedule.

In some embodiments, alisertib or a pharmaceutically acceptable salt thereof is administered on each of days 1, 2, 3, 8, 9, 10, 15, 16, and 17 of a 28 day schedule, and carboplatin is administered on day 1 of a 28 day schedule.

In some embodiments, alisertib or a pharmaceutically acceptable salt thereof is administered on each of days 1, 2, 3, 8, 9, 10, 15, 16, and 17 of a 28 day schedule, and cisplatin is administered on day 1 of a 28 day schedule.

In some embodiments, wherein the cancer is breast cancer, small cell lung cancer, or gastric cancer, the method comprises administering to a patient in need of such treatment a combination of alisertib or a pharmaceutically acceptable salt thereof and carboplatin or cisplatin.

In some embodiments, wherein the cancer is breast cancer, small cell lung cancer or gastric cancer, the method comprises administering to a patient in need of such treatment a combination of alisertib or a pharmaceutically acceptable salt thereof and cisplatin.

In some embodiments, wherein the cancer is small cell lung cancer, the method comprises administering to a patient in need of such treatment a combination of alisertib or a pharmaceutically acceptable salt thereof and cisplatin.

In some embodiments, wherein the cancer is breast cancer, small cell lung cancer or gastric cancer, the method comprises administering to a patient in need of such treatment a combination of alisertib or a pharmaceutically acceptable salt thereof and a platin, wherein alisertib or a pharmaceutically acceptable salt thereof is administered twice daily on each of days 1, 2, 3, 8, 9, 10, 15, 16, and 17 of a 28 day schedule, and the platin is administered on day 1 of a 28 day schedule.

In some embodiments, wherein the cancer is breast cancer, small cell lung cancer or gastric cancer, the method comprises administering to a patient in need of such treatment a combination of alisertib or a pharmaceutically acceptable salt thereof and a platin, wherein alisertib or a pharmaceutically acceptable salt thereof is administered from about 15 mg to about 50 mg per dose twice daily on each of days 1, 2, 3, 8, 9, 10, 15, 16, and 17 of a 28 day schedule, and the platin is administered from about 50 mg/mm$^2$ to about 70 mg/mm$^2$ on day 1 of a 28 day schedule.

In some embodiments, wherein the cancer is breast cancer, small cell lung cancer or gastric cancer, the method comprises administering to a patient in need of such treatment a combination of alisertib or a pharmaceutically acceptable salt thereof and cisplatin, wherein alisertib or a pharmaceutically acceptable salt thereof is administered from about 15 mg to about 50 mg per dose twice daily on each of days 1, 2, 3, 8, 9, 10, 15, 16, and 17 of a 28 day schedule, and cisplatin is administered from about 50 mg/mm$^2$ to about 70 mg/mm$^2$ on day 1 of a 28 day schedule.

Therapeutic Substance; Pharmaceutical Compositions.

Any of therapeutic agents described herein can be in the form of a pharmaceutically acceptable salt. In some embodiments, such salts are derived from inorganic or organic acids or bases. For reviews of suitable salts, see, e.g., Berge et al., *J. Pharm. Sci.*, 1977, 66, 1-19 and *Remington: The Science and Practice of Pharmacy,* 20th Ed., A. Gennaro (ed.), Lippincott Williams & Wilkins (2000).

Examples of suitable acid addition salts include acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, fumarate, lucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate and undecanoate.

Examples of suitable base addition salts include ammonium salts; alkali metal salts, such as sodium and potassium salts; alkaline earth metal salts, such as calcium and magnesium salts; salts with organic bases, such as dicyclohexylamine salts, N-methyl-D-glucamine; and salts with amino acids such as arginine, lysine, and the like.

For example, Berge lists the following FDA-approved commercially marketed salts: anions acetate, besylate (benzenesulfonate), benzoate, bicarbonate, bitartrate, bromide, calcium edetate (ethylenediaminetetraacetate), camsylate (camphorsulfonate), carbonate, chloride, citrate, dihydrochloride, edetate (ethylenediaminetetraacetate), edisylate (1,2-ethanedisulfonate), estolate (lauryl sulfate), esylate (ethanesulfonate), fumarate, gluceptate (glucoheptonate), gluconate, glutamate, glycollylarsanilate (glycollamidophenylarsonate), hexylresorcinate, hydrabamine (N,N'-di(dehydroabietyl)ethylenediamine), hydrobromide, hydrochloride, hydroxynaphthoate, iodide, isethionate (2-hydroxyethanesulfonate), lactate, lactobionate, malate, maleate, mandelate, mesylate (methanesulfonate), methylbromide, methylnitrate, methylsulfate, mucate, napsylate (2-naphthalenesulfonate), nitrate, pamoate (embonate), pantothenate, phosphate/diphosphate, polygalacturonate, salicylate, stearate, subacetate, succinate, sulfate, tannate, tartrate, teoclate (8-chlorotheophyllinate) and triethiodide; organic cations benzathine (N,N'-dibenzylethylenediamine), chloroprocaine, choline, diethanolamine, ethylenediamine, meglumine (N-methylglucamine) and procaine; and metallic cations aluminum, calcium, lithium, magnesium, potassium, sodium and zinc.

Berge additionally lists the following non-FDA-approved commercially marketed (outside the United States) salts: anions adipate, alginate, aminosalicylate, anhydromethylenecitrate, arecoline, aspartate, bisulfate, butylbromide, camphorate, digluconate, dihydrobromide, disuccinate, glycerophosphate, hemisulfate, hydrofluoride, hydroiodide, methylenebis(salicylate), napadisylate (1,5-naphthalenedisulfonate), oxalate, pectinate, persulfate, phenylethylbarbiturate, picrate, propionate, thiocyanate, tosylate and undecanoate; organic cations benethamine (N-benzylphenethylamine), clemizole (1-p-chlorobenzyl-2-pyrrolidine-1'-ylmethylbenzimidazole), diethylamine, piperazine and tromethamine (tris(hydroxymethyl)aminomethane); and metallic cations barium and bismuth.

As used herein, "pharmaceutically acceptable carrier" refers to a material that is compatible with a recipient subject (a human) and is suitable for delivering an active agent to the target site without terminating the activity of the agent. The toxicity or adverse effects, if any, associated with the carrier preferably are commensurate with a reasonable risk/benefit ratio for the intended use of the active agent.

The pharmaceutical compositions for use in the methods of the present disclosure can be manufactured by methods well known in the art such as conventional granulating, mixing, dissolving, encapsulating, lyophilizing, or emulsifying processes, among others. Compositions can be produced in various forms, including granules, precipitates, or particulates, powders, including freeze dried, rotary dried or spray dried powders, amorphous powders, tablets, capsules, syrup, suppositories, injections, emulsions, elixirs, suspensions or solutions. Formulations can contain stabilizers, pH modifiers, surfactants, solubilizing agents, bioavailability modifiers and combinations of these.

Pharmaceutically acceptable carriers that can be used in these compositions include ion exchangers, alumina, aluminum stearate, lecithin, serum proteins, such as human serum albumin, buffer substances such as phosphates or carbonates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

These pharmaceutical compositions are formulated for pharmaceutical administration to a human being. Such compositions can be administered orally, parenterally, by inhalation spray, topically, rectally, nasally, buccally, vaginally or via an implanted reservoir. The term "parenteral" as used herein includes subcutaneous, intravenous, intraperitoneal, intramuscular, intra-articular, intra-synovial, intrasternal, intrathecal, intrahepatic, intralesional and intracranial injection or infusion techniques. In some embodiments, the compositions are administered orally, intravenously or subcutaneously. In some embodiments, the compositions are administered orally. In some embodiments, the compositions are administered intravenously. These formulations can be designed to be short-acting, fast-releasing, or long-acting. Furthermore, the compositions can be administered in a local rather than systemic means, such as administration (e.g., by injection) at a tumor site.

Pharmaceutical formulations can be prepared as liquid suspensions or solutions using a liquid, such as an oil, water, an alcohol, and combinations of these. Solubilizing agents such as cyclodextrins can be included. Pharmaceutically suitable surfactants, suspending agents, or emulsifying agents, can be added for oral or parenteral administration. Suspensions can include oils, such as peanut oil, sesame oil, cottonseed oil, corn oil and olive oil. Suspension preparations can also contain esters of fatty acids such as ethyl oleate, isopropyl myristate, fatty acid glycerides and acetylated fatty acid glycerides. Suspension formulations can include alcohols, such as ethanol, isopropyl alcohol, hexadecyl alcohol, glycerol and propylene glycol; ethers, such as poly(ethyleneglycol); petroleum hydrocarbons such as mineral oil and petrolatum; and water.

Sterile injectable forms of these pharmaceutical compositions can be aqueous or oleaginous suspensions. These suspensions may be formulated according to techniques known in the art using suitable dispersing or wetting agents and suspending agents. The sterile injectable preparation can also be a sterile injectable solution or suspension in a non-toxic parenterally acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose, any bland fixed oil can be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as sorbitan alkyl esters, such as Tweens or Spans, and other emulsifying agents or bioavailability enhancers which are commonly used in the manufacture of pharmaceutically acceptable solid, liquid, or other dosage forms can also be used for the purposes of formulation. Compounds can be formulated for parenteral administration by injection such as by bolus injection or continuous infusion. A unit dosage form for injection can be in ampoules or in multi-dose containers.

These pharmaceutical compositions can be orally administered in any orally acceptable dosage form including capsules, tablets, aqueous suspensions or solutions. When aqueous suspensions are required for oral use, the active ingredient is combined with emulsifying and suspending agents. If desired, certain sweetening, flavoring or coloring agents can also be added. For oral administration in a capsule form, useful diluents include lactose and dried cornstarch. In the case of tablets for oral use, carriers that are commonly used include lactose and corn starch. Lubricating agents, such as magnesium stearate, are also typically added. Coatings may be used for a variety of purposes, e.g., to mask taste, to affect the site of dissolution or absorption, or to prolong drug action. Coatings can be applied to a tablet or to granulated particles for use in a capsule.

Alternatively, these pharmaceutical compositions can be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

These pharmaceutical compositions can also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract may be effected in a rectal suppository formulation (see above) or in a suitable enema formulation. Topically-transdermal patches can also be used. For topical applications, the pharmaceutical compositions can be formulated in a suitable ointment containing the active component suspended or dissolved in one or more carriers. Carriers for topical administration of the compounds of the present disclosure include mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active component(s) suspended or dissolved in one or more pharmaceutically acceptable carriers. Suitable carriers include mineral oil, sorbitan monostearate, polysorbate 60, cetyl esters wax, cetearyl alcohol, 2-octyldodecanol, benzyl alcohol and water.

For ophthalmic use, the pharmaceutical compositions can be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions can be formulated in an ointment such as petrolatum.

The pharmaceutical compositions can also be administered by nasal aerosol or inhalation. Such compositions are prepared according to techniques well known in the art of pharmaceutical formulation and can be prepared as solutions in saline, employing benzyl alcohol or other suitable preservatives, absorption promoters to enhance bioavailability, fluorocarbons, and/or other conventional solubilizing or dispersing agents.

In some embodiments, the methods of the present disclosure further comprise administering a anti-cancer agent. As used herein, the term "anticancer agent" refers to any agent that is administered to a subject with cancer for purposes of treating the cancer. The administration of the further anti-cancer agent includes administration concurrently or sequentially with the combinations of the present disclosure. Alternatively, the further anti-cancer agent can be combined into one composition with the combinations of the present disclosure which is administered to the patient.

Non-limiting examples of anti-cancer agents include DNA damaging chemotherapeutic agents such as topoisomerase I inhibitors (e.g., irinotecan, topotecan, camptothecin and analogs or metabolites thereof); topoisomerase II inhibitors (e.g., etoposide, and teniposide); anthracyclines (e.g. doxorubicin, daunorubicin and idarubicin) alkylating agents (e.g., melphalan, chlorambucil, busulfan, thiotepa, ifosfamide, carmustine, lomustine, semustine, streptozocin, decarbazine, methotrexate, pemetrexed, mitomycin C, and cyclophosphamide); DNA intercalators; DNA intercalators and free radical generators such as bleomycin; and nucleoside mimetics (e.g., 5-fluorouracil, capecitibine, fludarabine, cytarabine, mercaptopurine, thioguanine, pentostatin, and hydroxyurea). Chemotherapeutic agents that disrupt cell replication include: vincristine, vinblastin, and related analogs; thalidomide, lenalidomide, and related analogs (e.g., CC-5013 and CC-4047); protein tyrosine kinase inhibitors (e.g., imatinib mesylate, erlotonib, croztinib and gefitinib); proteasome inhibitors (e.g., bortezomib); NF-κB inhibitors, including inhibitors of IκB kinase; antibodies which bind to proteins overexpressed in cancers and thereby downregulate cell replication (e.g., trastuzumab, panitumumab, rituximab, cetuximab, and bevacizumab); and other inhibitors of proteins or enzymes known to be upregulated, over-expressed or activated in cancers, the inhibition of which downregulates cell replication.

Kits

In some embodiments, alisertib or platin described herein can be manufactured for inclusion in a kit. A "kit" is any article of manufacture (e.g., a package or container) comprising at least one reagent or chemotherapeutic agent. A kit for use in the methods herein can comprise an Aurora kinase inhibitor, such as alisertib or a pharmaceutically acceptable salt thereof. In some embodiments, the kit can further include a platin. In some embodiments, the kit can include alisertib or a pharmaceutically acceptable salt thereof and carboplatin. In some embodiments, the kit can include alisertib or a pharmaceutically acceptable salt thereof and cisplatin.

In some embodiments, a kit comprising alisertib or a pharmaceutically acceptable salt thereof and a platin can further include another component or reagent. In some embodiments, a reagent in the kit can be a diluent for preparing the alisertib or a pharmaceutically acceptable salt thereof for administration. In some embodiments, a reagent in the kit can be a diluent for preparing the platin for administration. In some embodiments, a component in the kit can be a vessel for mixing the combination of alisertib and the platin. In some embodiments, the kit can include instructions for calculating the dose of each therapeutic component of the kit. In some embodiments, the instructions can include the Calvert formula.

In order that this present disclosure be more fully understood, the following examples are set forth. These examples are illustrative only and are not intended to limit the scope of the present disclosure in any way.

EXAMPLES

Abbreviations h hour
min minutes
HPLC High-pressure liquid chromatography
UPLC Ultra-pressure liquid chromatography
NMR Nuclear Magnetic Resonance
THF tetrahydrofuran WFI Water for Injection
TGI tumor growth inhibition
mg milligram
mm³ cubic millimeter
HPBCD 2-hydroxypropyl-β-cyclodextrin
SC subcutaneously
SD starting day Example 1: In Vivo Tumor Efficacy Models Xenograft Models NCI-H82 1: A thirty-to-forty mg fragment of NCI-H82 small cell lung tumor, propagated in an in vivo passage, was implanted SC in the area of the right flank of female Athymic NCr nu/nu mice (age 5 weeks, Charles River Laboratories, Wilmington, MA) using a 12-gauge trocar needle. Tumors were allowed to reach 100-245 mm³ in volume before the start of treatment. A sufficient number of mice were implanted so that tumors in a volume range as narrow as possible were selected for the trial on the day of treatment initiation (day 13 after tumor implantation, designated as SD, or Day 0). Those animals selected with tumors in the proper volume range were randomized into 9 treatment and control groups (n=10/group) so that the median tumor volumes on the first day of treatment were as close as possible (206-219 mm³).

NCI-H82 2: A thirty-to-forty mg fragment of NCI-H82 small cell lung tumor, propagated in an in vivo passage, was implanted SC in the area of the right flank of female Athymic NCr nu/nu mice (age 5 weeks, Charles River Laboratories, Wilmington, MA) using a 12-gauge trocar needle. Tumors were allowed to reach 100-245 mm³ in volume before the start of treatment. A sufficient number of mice were implanted so that tumors in a volume range as narrow as possible were selected for the trial on the day of treatment initiation (day 14 after tumor implantation, designated as SD, or Day 0). Those animals selected with tumors in the proper volume range were randomized into 9 treatment and control groups (n=10/group) so that the median tumor volumes on the first day of treatment were as close as possible (196-198 mm³).

NCI-H69: A thirty-to-forty mg fragment of NCI-H69 small cell lung tumor, propagated in an in vivo passage, was implanted SC in the area of the right flank of female Athymic NCr nu/nu nice (age 6 weeks, Charles River Laboratories, Frederick, MD) using a 12-gauge trocar needle. Tumors were allowed to reach 100-245 mm³ in volume before the start of treatment. A sufficient number of mice were implanted so that tumors in a volume range as narrow as possible were selected for the trial on the day of treatment initiation (day 24 after tumor implantation, designated as SD, or Day 0). Those animals selected with tumors in the proper volume range were randomized into 9 treatment and control groups (n=10/group) so that the mean tumor volumes on the first day of treatment were as close as possible (169-174 mm³).

Test Agents

An 8 mg/mL suspension of alisertib was formulated weekly by adding a half volume of 20% HPBCD in water for injection (WFI) to the alisertib powder, then mixing by vortexing, and sonicating for one minute. The suspension was diluted to 4 mg/mL with 2% sodium bicarbonate (NaHCO₃) in WFI. The final composition of the alisertib vehicle was 10% HPBCD/1% NaHCO₃ in WFI. The 4 mg/mL solution was diluted to 2 mg/mL with complete vehicle for the lower dose. The alisertib dosing formulations were stored in brown bottles at room temperature during the dosing period. All alisertib injections were administered on the basis of exact animal body weight on each day of treatment, using an injection volume of 0.05 mL/10 g body weight.

A 10 mg/mL stock solution of carboplatin (Hospira, Inc.) was diluted each day of treatment with saline. Carboplatin injections were administered on the basis of exact animal body weight on each day of treatment, using an injection volume of 0.10 mL/10 g body weight.

A 1 mg/mL stock solution of cisplatin (Cisplatin Injection, PCH PHAMACHEMIE) was diluted each day of treatment with saline to 0.8 and 0.4 mg/mL. Cisplatin injections were administered on the basis of exact animal body weight on each day of treatment, using an injection volume of 0.05 mL/10 g body weight.

Tumor Measurements

Tumors were measured twice weekly using vernier calipers. Tumor volumes were calculated using standard procedures $V=W^2 \times L/2$). When mean tumor volumes reached approximately 206-219 mm³ for NCI-H82 1, 196-198 mm³ for NCI-H82 2, or 169-174 mm³ for NCI-H69, mice were randomized into groups of n=10/arm as described in the tables below, and injected with vehicle, alisertib or agents (cisplatin, or carboplatin), or the combination of alisertib plus one of the agents, at various doses and schedules as described below in Tables 1a, 2a and 3a. Tumor size and body weight were measured approximately twice a week for the duration of the study. Mice are euthanized when their tumor volume reached 10% of their body weight, or when the average tumor volume of a treatment or control group reached approximately 2000 mm³. Tumor growth continued to be monitored after the dosing period in some studies. Tumor volumes on study Days 20 or 21 from the day of treatment initiation are shown in Tables 1a, 2a and 3a. Average tumor volume is reported as a function of time for selected arms of selected studies in FIGS. 1, 2 and 3.

Statistical Analyses of Combination Effect for Tumor Growth in Subcutaneous Xenograft Models Measurements from the day of treatment initiation to Day 20 or Day 21 following treatment initiation are analyzed as specified in Tables below. All tumor volumes have a value of 1 added to them before $\log_{10}$ transformation. For each animal, the log tumor volume at the day of treatment initiation is subtracted from the log tumor volume on the subsequent days. This difference vs. time is used to calculate an area under the curve (AUC) for each animal using the trapezoid rule. In instances when an animal in a treatment group is removed early from the study, the last observed tumor value is carried forward through all subsequent time points. The synergy score for the combination of agents A and B is defined as $$100*(\text{mean}(AUC_{AB})-\text{mean}(AUC_A)-\text{mean}(AUC_B)+\text{mean}(AUC_{ctl}))/\text{mean}(AUC_{ctl}):$$

where $AUC_{AB}$, $AUC_A$, $AUC_B$, and $AUC_{ctl}$ are the AUC values for animals in the combination group, the A group, the B group, and the control group, respectively. The standard error of the synergy score is computed based on the variation in the AUC values among the animals. A two sided t-test is used to determine if the synergy score is significantly different from zero. If the P-value is above 0.05, then the combination is considered to be additive. If the P-value is below 0.05, and the synergy score is less than zero, then the combination is considered to be synergistic. If the P-value is below 0.05 and the synergy score was greater than zero, but the mean AUC for the combination was lower than the lowest mean AUC among the two single agent treatments, then the combination was sub-additive. If the P-value is below 0.05 and if the synergy score was greater than zero, and the mean AUC for the combination was greater than the mean AUC for at least one of the single agent treatments, then the combination was antagonistic.

Results

Mouse xenograft models, performed as described in the general methods above, were used to assess the combination effect in vivo of alisertib and cisplatin, and alisertib and carboplatin. The details for each study are as shown below in Tables 1a, 2a and 3a. The results were analyzed using the statistical analysis described above and the classification of the combination is shown below in Tables 1b, 2b and 3b.

Alisertib and Carboplatin

NCI-H82 Xenograft Model Study 1

In the NCI-H82 small cell lung turner xenograft model, treatments began on day 13 following tumor implantation (Day 0) for all groups. Alisertib was tested at doses of 20 and 10 mg/kg administered PO on a QDx21 (once daily for 21 consecutive days) schedule. Carboplatin was tested at doses of 75 and 25 mg/kg administered IP on a Q7Dx3 (once weekly for 3 weeks) schedule. In the combination treatment groups alisertib was administered first, followed immediately by the administration of carboplatin. One group served as a vehicle-treated control group (Group 1) receiving PO treatment with the vehicle used for administration of alisertib in treatment groups on a QDx21 schedule.

Figure 1:
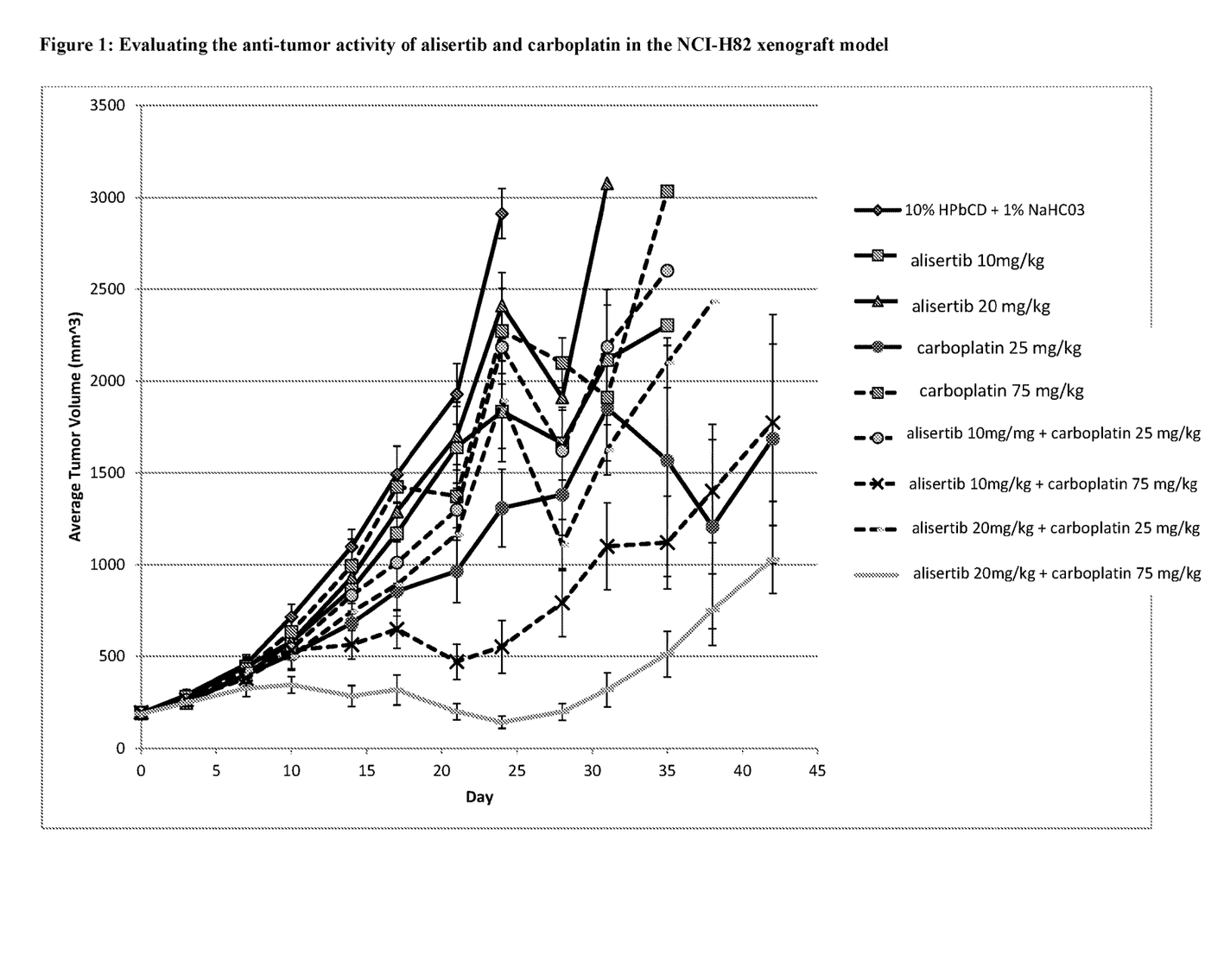
FIG. 1 shows the anti-tumor activity of alisertib and carboplatin in the NCI-H82 xenograft model.

The combination arms of alisertib with carboplatin yielded additive to synergistic anti-tumor effects. The treatment groups from the study are shown in Table 1a. The combination effect for this combination is shown in Table 1b. Tumor growth curves are shown during the treatment period (FIG. 1). Error bars shown in FIG. 1 indicate the standard error of the mean (SEM).

TABLE 1a

Combination of carboplatin and alisertib in the NCI-H82 xenograft model

| Study Group | Treatment | Dosing Regimen | Route | Tumor Volume Day 21 | SEM Tumor Volume Day 21 | Number of mice in group (number on Day 21) |
|---|---|---|---|---|---|---|
| 1 | 10% HPBCD/1% NaHCO3 in WFI | QDx21 | PO | 1805 | 124 | 8 |
| 2 | 20 mg/kg Alisertib | QDx21 | PO | 1640 | 224 | 9 |
| 3 | 10 mg/kg Alisertib | QDx21 | PO | 1701 | 186 | 9 |
| 4 | 75 mg/kg Carboplatin | Q7Dx3 | IP | 965 | 169 | 10 |
| 5 | 25 mg/kg Carboplatin | Q7Dx3 | IP | 1373 | 171 | 7 |

TABLE 1a-continued

Combination of carboplatin and alisertib in the NCI-H82 xenograft model

| Study Group | Treatment | Dosing Regimen | Route | Tumor Volume Day 21 | SEM Tumor Volume Day 21 | Number of mice in group (number on Day 21) |
|---|---|---|---|---|---|---|
| 6 | 20 mg/kg Alisertib, 75 mg/kg Carboplatin | QDx21; Q7Dx3 | PO; IP | 199 | 44 | 10 |
| 7 | 20 mg/kg Alisertib, 25 mg/kg Carboplatin | QDx21; Q7Dx3 | PO; IP | 1166 | 180 | 10 |
| 8 | 10 mg/kg Alisertib, 75 mg/kg Carboplatin | QDx21; Q7Dx3 | PO; IP | 472 | 96 | 10 |
| 9 | 10 mg/kg Alisertib, 25 mg/kg Carboplatin | QDx21; Q7Dx3 | PO; IP | 1299 | 145 | 10 |

TABLE 1b

Classification for in vivo combination of carboplatin and alisertib in the NCI-H82 xenograft model

| Treatment | Synergy score | SEM | P-value | Classification |
|---|---|---|---|---|
| 10 mg/kg Alisertib + 25 mg/kg carboplatin | −2.3 | 7.3 | 0.758 | Additive |
| 10 mg/kg Alisertib + 75 mg/kg carboplatin | −2.5 | 11.7 | 0.836 | Additive |
| 20 mg/kg Alisertib + 25 mg/kg carboplatin | −2.1 | 9.3 | 0.823 | Additive |
| 20 mg/kg Alisertib + 75 mg/kg carboplatin | −31.0 | 13.1 | 0.027 | Synergy |

Alisertib and Cisplatin

NCI-H82 Xenograft Model Study 2

In the NCI-H82 small cell lung tumor xenograft model, treatments began on day 14 following tumor implantation (Day 0) for all groups. Alisertib was tested at doses of 20 and 10 mg/kg administered PO on a QDx21 (once daily for 21 consecutive days) schedule. Cisplatin was tested at doses of 4 and 2 mg/kg administered IP on Q4Dx3 (once every 4 days for 3 injections) schedule. In the combination treatment groups alisertib was administered first, followed immediately by the administration of cisplatin. One group served as a vehicle-treated control group (Group 1) receiving PO treatment with the vehicle used for administration of alisertib in treatment groups on a QDx21 schedule.

Figure 2:
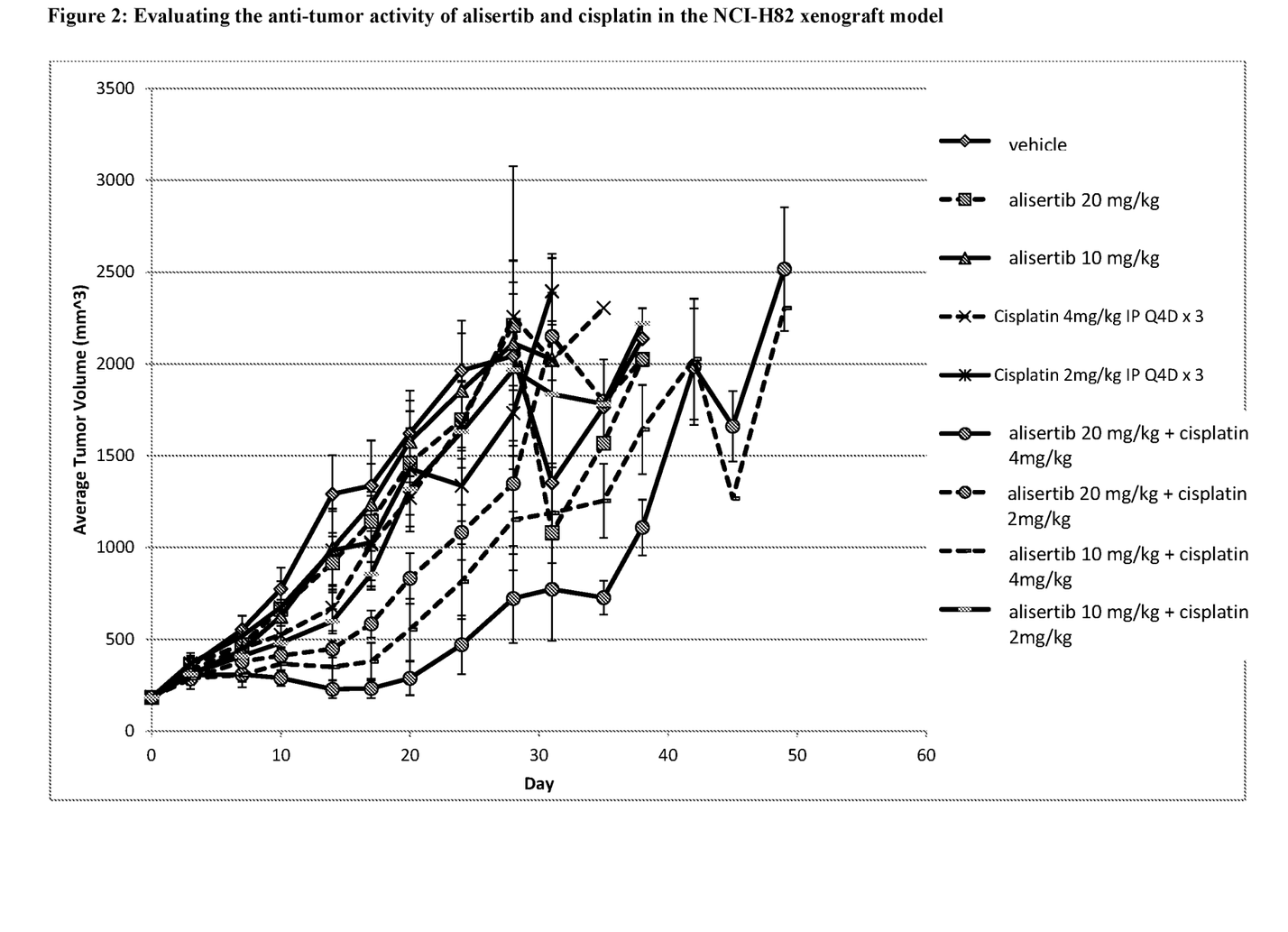
FIG. 2 shows the anti-tumor activity of alisertib and cisplatin in the NCI-H82 xenograft model.

The combination arms of alisertib with cisplatin yielded additive to synergistic anti-tumor effects. The treatment groups from the study are shown in Table 2a. The combination benefit for this combination is shown in Table 2b. Tumor growth curves are shown during the treatment period (FIG. 2). Error bars shown in FIG. 2 indicate the standard error of the mean (SEM).

TABLE 2a

Combination of cisplatin and alisertib in the NCI-H82 xenograft model

| Study Group | Treatment | Dosing Regimen | Route | Tumor Volume Day 20 | SEM Tumor Volume Day 20 | Number of mice in group (number on Day 20) |
|---|---|---|---|---|---|---|
| 1 | 10% HPBCD/1% NaHCO3 in WFI | QDx21 | PO | 1622 | 233 | 8 |
| 2 | 20 mg/kg Alisertib | QDx21 | PO | 1461 | 189 | 8 |
| 3 | 10 mg/kg Alisertib | QDx21 | PO | 1578 | 223 | 8 |
| 4 | 4 mg/kg Cisplatin | Q4Dx3 | IP | 1270 | 182 | 8 |
| 5 | 2 mg/kg Cisplatin | Q4Dx3 | IP | 1429 | 314 | 7 |
| 6 | 20 mg/kg Alisertib, 4 mg/kg Cisplatin | QDx21; Q4Dx3 | PO; IP | 287 | 92 | 10 |
| 7 | 20 mg/kg Alisertib, 2 mg/kg Cisplatin | QDx21; Q4Dx3 | PO; IP | 832 | 138 | 10 |
| 8 | 10 mg/kg Alisertib, 4 mg/kg Cisplatin | QDx21; Q4Dx3 | PO; IP | 553 | 169 | 10 |
| 9 | 10 mg/kg Alisertib, 2 mg/kg Cisplatin | QDx21; Q4Dx3 | PO; IP | 1318 | 139 | 10 |

TABLE 2b

Classification for in vivo combination of cisplatin and alisertib in the NCI-H82 xenograft model

| Treatment | Synergy score | SEM | P-value | Classification |
|---|---|---|---|---|
| 20 mg/kg Alisertib + 4 mg/kg cisplatin | −39.2 | 12.3 | 0.004 | Synergy |
| 20 mg/kg Alisertib + 2 mg/kg cisplatin | −17.7 | 12.0 | 0.153 | Additive |
| 10 mg/kg Alisertib + 4 mg/kg cisplatin | −28.1 | 14.7 | 0.067 | Additive |
| 10 mg/kg Alisertib + 2 mg/kg cisplatin | −0.2 | 11.1 | 0.987 | Additive |

NCI-H69 Xenograft Model

In the NCI-H69 small cell lung turner xenograft model, treatments began on day 24 following tumor implantation (Day 0) for all groups. Alisertib was tested at doses of 20 and 10 mg/kg administered PO on a QDx21 schedule. Cisplatin was tested at doses of 4 and 2 mg/kg administered IP on a Q4Dx3 schedule. In the combination treatment groups alisertib was administered first, followed immediately by the administration of cisplatin. One group served as a vehicle-treated control group (Group 1) receiving PO treatment with the vehicle used in the administration of alisertib in treatment groups on a QDx21 schedule.

Figure 3:
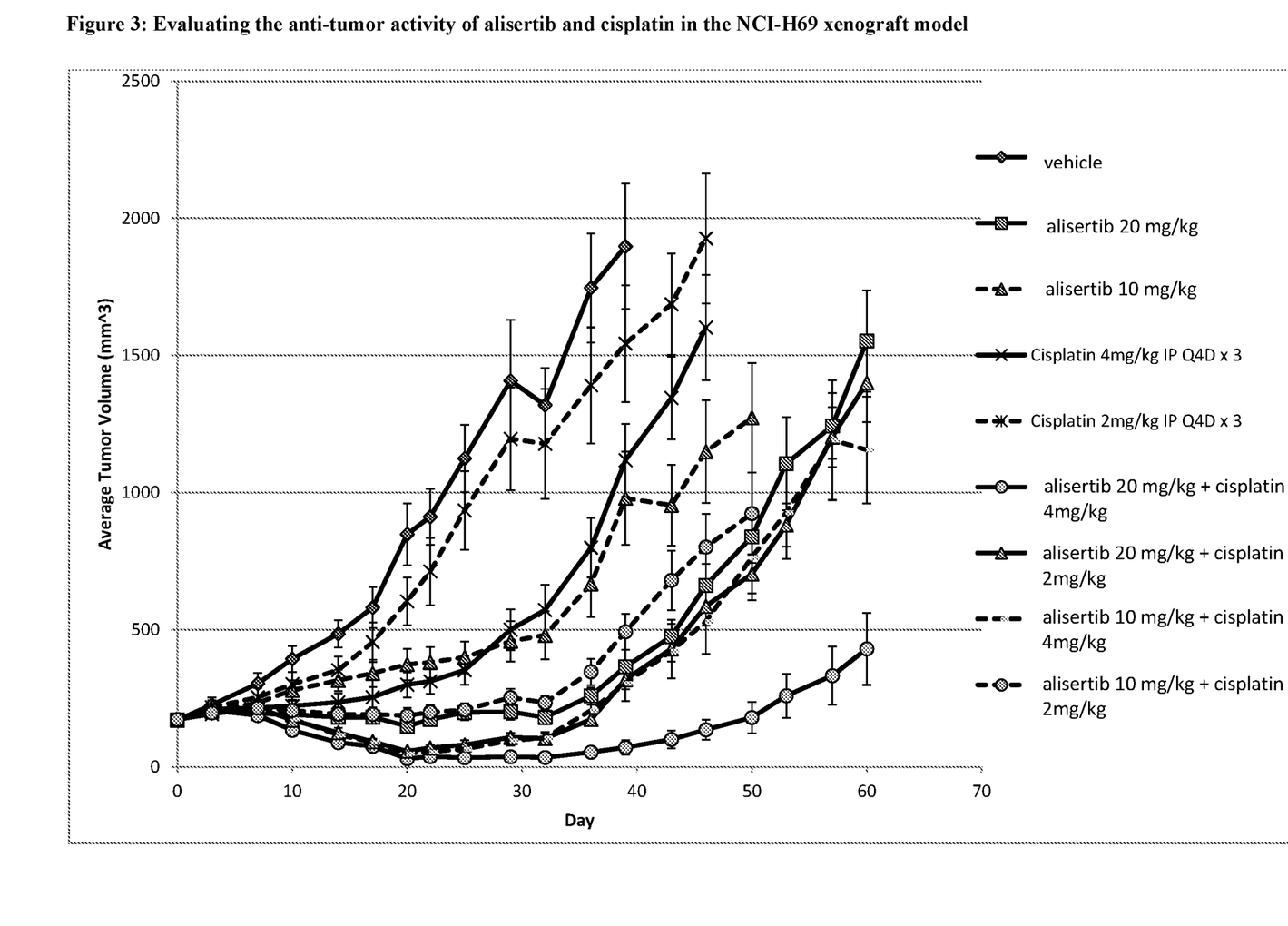
FIG. 3 shows the anti-tumor activity of alisertib and cisplatin in the NCI-69 xenograft model.

The combination treatment using these doses and schedules led to additive combination effects. The treatment groups from the study are shown in Table 3a. The combination benefit for this combination in this study was scored and is shown in Table 3b. Tumor growth curves are shown during the treatment period (FIG. 3). Error bars shown in FIG. 3 indicate the standard error of the mean (SEM).

TABLE 3a

Combination of cisplatin and alisertib in the NCI-H69 xenograft model

| Study Group | Treatment | Dosing Regimen | Route | Tumor Volume Day 20 | SEM Tumor Volume Day 20 | Number of mice in group (number on Day 20) |
|---|---|---|---|---|---|---|
| 1 | 10% HPBCD/1% NaHCO3 in WFI | QDx21 | PO | 848 | 112 | 10 |
| 2 | 20 mg/kg Alisertib | QDx21 | PO | 149 | 22 | 10 |
| 3 | 10 mg/kg Alisertib | QDx21 | PO | 374 | 57 | 10 |
| 4 | 4 mg/kg Cisplatin | Q4Dx3 | IP | 300 | 45 | 10 |
| 5 | 2 mg/kg Cisplatin | Q4Dx3 | IP | 604 | 87 | 10 |
| 6 | 20 mg/kg Alisertib, 4 mg/kg Cisplatin | QDx21; Q4Dx3 | PO; IP | 30 | 8 | 10 |
| 7 | 20 mg/kg Alisertib, 2 mg/kg Cisplatin | QDx21; Q4Dx3 | PO; IP | 57 | 9 | 10 |
| 8 | 10 mg/kg Alisertib, 4 mg/kg Cisplatin | QDx21; Q4Dx3 | PO; IP | 49 | 9 | 10 |
| 9 | 10 mg/kg Alisertib, 2 mg/kg Cisplatin | QDx21; Q4Dx3 | PO; IP | 187 | 29 | 10 |

TABLE 3b

Classification for in vivo combination of cisplatin and alisertib in the NCI-H69 xenograft model

| Treatment | Synergy score | SEM | P-value | Classification |
|---|---|---|---|---|
| 20 mg/kg Alisertib + 4 mg/kg Cisplatin | −0.4 | 16.2 | 0.980 | Additive |
| 20 mg/kg Alisertib + 2 mg/kg Cisplatin | −4.5 | 12.9 | 0.731 | Additive |
| 10 mg/kg Alisertib + 4 mg/kg Cisplatin | −13.0 | 13.0 | 0.327 | Additive |
| 10 mg/kg Alisertib + 2 mg/kg Cisplatin | −13.9 | 12.5 | 0.275 | Additive |

What is claimed is:

1. A method of treating small cell lung cancer, comprising administering to a patient having the small cell lung cancer a combination consisting of 4-{[9-chloro-7-(2-fluoro-6-methoxyphenyl)-5H-pyrimido[5,4-d][2]benzazepin-2-yl]amino}-2-methoxybenzoic acid or a pharmaceutically acceptable salt thereof, and a platin,
wherein 4-{[9-chloro-7-(2-fluoro-6-methoxyphenyl)-5H-pyrimido[5,4-d][2]benzazepin-2-yl]amino}-2-methoxybenzoic acid or a pharmaceutically acceptable salt thereof is administered at about 48.6 mg per dose twice daily;
wherein the platin is cisplatin or carboplatin, wherein cisplatin is administered at about 12 mg/m$^2$ per day, or carboplatin is administered at an AUC (area under the plasma concentration versus time curve) of about 4.6 mg/mL/min; and provided that 4-{[9-chloro-7-(2-fluoro-6-methoxyphenyl)-5H-pyrimido[5,4-d][2]benzazepin-2-yl]amino}-2-methoxybenzoic acid or a pharmaceutically acceptable salt thereof and the platin are the only active ingredients used in the method.

2. The method of claim 1, wherein 4-{[9-chloro-7-(2-fluoro-6-methoxyphenyl)-5H-pyrimido[5,4-d][2]benzazepin-2-yl]amino}-2-methoxybenzoic acid or a pharmaceutically acceptable salt thereof is administered twice a day on each of days 1, 2, 3, 8, 9, 10, 15, 16, and 17 of a 28 day schedule.

3. The method of claim 1, wherein the platin is administered on day 1 of a 28 day schedule.

4. The method of claim 1, wherein the platin is administered on each of days 1, 8 and 15 of a 28 day schedule.

5. The method of claim 1, wherein the platin is cisplatin.

6. The method of claim 1, wherein the platin is carboplatin.

7. The method of claim 1, wherein 4-{[9-chloro-7-(2-fluoro-6-methoxyphenyl)-5H-pyrimido[5,4-d][2]benzazepin-2-yl]amino}-2-methoxybenzoic acid or a pharmaceutically acceptable salt thereof and the platin are administered sequentially.

8. The method of claim 1, wherein 4-{[9-chloro-7-(2-fluoro-6-methoxyphenyl)-5H-pyrimido[5,4-d][2]benzazepin-2-yl]amino}-2-methoxybenzoic acid or a pharmaceutically acceptable salt thereof and the platin are administered simultaneously.

9. The method of claim 1, wherein 4-{[9-chloro-7-(2-fluoro-6 -methoxyphenyl)-5H-pyrimido[5,4-d][2]benzazepin-2-yl]amino}-2-methoxybenzoic acid or a pharmaceutically acceptable salt thereof is administered orally.

10. The method of claim 1, wherein the platin is administered intravenously.

* * * * *